United States Patent [19]

Van den Berg et al.

[11] Plant 4,725

[45] May 26, 1981

[54] IMPATIENS PLANT

[75] Inventors: Cornelis P. Van den Berg; James C. Mikkelsen, both of Ashtabula, Ohio

[73] Assignee: Mikkelsens Inc., Ashtabula, Ohio

[21] Appl. No.: 103,085

[22] Filed: Dec. 12, 1979

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

An impatiens plant known by the cultivar name Halo, and particularly characterized by the combined characteristics of good self-branching; spreading habit; highly variegated foliage; bright orange and large flowers; early flowering; suitability for growing both outside in full sunlight and in hanging baskets; and by its good keeping quality both outside in full sunlight and in hanging baskets.

1 Drawing Figure

The present invention relates to a new and distinct cultivar of impatiens plant, hereinafter referred to by the cultivar name Halo.

Halo is the product of a planned breeding program and was originated from a cross made by us in Ashtabula, Ohio. The seed parent was an unnamed cultivar identified by seedling number 76-377-5, and the pollen parent was Satellite, a commercial but unpatented cultivar. Asexual reproduction by terminal or stem cuttings taken by us in Ashtabula, Ohio has shown that the combination of unique characteristics as herein disclosed for Halo are stable and retained through successive generations of asexual reproduction.

The following characteristics distinguish Halo from both its parent varieties and other cultivated impatiens of this type known and used in the floriculture industry:

1. Halo was selected especially for its flower color, flower size, earliness of flowering, floriferousness, and a spreading habit, which makes the cultivar suitable for growing in hanging baskets.
2. Flowers are bright orange, appear in an early stage of plant development, and the plant continues to flower abundantly throughout the growing season.
3. Flowers are 60 mm. in diameter, larger than those of Sunfire and Satellite. Sunfire is a new cultivar of the present inventors and disclosed in pending application Ser. No. 103,090, filed Dec. 12, 1979.
4. Leaf size, leaf shape and leaf variegation are comparable to that of Sunfire.
5. Superior self-branching habit.
6. Speading habit and good self-branching make plant high suitable for growing in hanging baskets.
7. Cultivar exhibits good keeping qualities both in hanging baskets and if grown outside in full sunlight in Ashtabula, Ohio where it will flower from planting date in early June until frost kills the plant.
8. Growth rate is comparable to that of Sunfire, producing a dome-shaped plant 30 cm. high and 60 cm. in diameter in 60 days after planting outside, starting from a plant in a 10 cm. pot; or a saleable 8" to 10" hanging basket, starting from 3 rooted cuttings per basket, in approximately 90 days, both as tested in Ashtabula, Ohio.

The accompanying colored photograph illustrates the flowers and foliage of Halo, with the colors being as true as it is reasonably possible to obtain in a colored reproduction of this type. It should be noted that the actual flower color is brighter orange than the photograph, and the foliage is lighter green than shown in the photograph. The color values stated below for the flowers and foliage are, however, correct.

The following is a detailed description of the new impatiens cultivar based on plants produced under commercial practices in Ashtabula, Ohio in the greenhouses of Mikkelsens Inc. and outdoors in full sunlight. Color references are made to the Royal Horticultural Society Colour Chart except where general terms of ordinary dictionary significance are used.

Parentage: A controlled cross of Mikkelsen seedling number 76-377-5 as the seed parent and the cultivar Satellite as the pollen parent.

Propagation:

(A) *Type cutting.*—Short tip cutting with stems up to 2 cm. long.

(B) *Time to root.*—10–12 days at 20° C., summer. 14–16 days at 20° C., winter.

(C) *Rooting habit.*—Abundant, fibrous.

Plant description:

(A) *Form.*—Spreading, close internoded, self-branching herb, producing a dome-shaped plant approximately 30 cm. high and 60 cm. in diameter when grown outside, starting from a 10 cm. pot, in approximately 60 days.

(B) *Habit of growth.*—Rate of growth moderate for this type of plant. Vegetative shoots are formed at the lower nodes and flowers at the higher nodes.

(C) *Foliage description.*—Lower leaves opposite, higher leaves in whorls of 3 up to 10. Leaves are simple. (1) Size: Average full grown leaf 115 mm. long × 34 mm. wide. Full grown leaves have very short to no petioles; young leaves have no petioles. (2) Shape: Elliptic, apex acute to acuminate, base attenuate. (3) Texture: Leathery, glabrous. (4) Margin: Ciliate to very slightly serrulate. (5) Color: Young foliage; top side yellow green 147A; under side green 138 B-C. Mature foliage; top side outer area yellow green 147A, inner area yellow 11A; under side outer area green 138B, inner area yellow 12C. (6) Veination: Pinnate, main vein red 47B.

Flowering description:

(A) *Flowering habits.*—Very floriferous, flowers occurring progressively around the whorl of leaves. Flowers are large and single.

(B) *Natural flowering season.*—Flowering is indeterminate and occurs throughout the year.

(C) *Flower buds.*—Conical, covered with 3 sepals. Upper 2 sepals are 11 mm. long × 5 mm. wide, acuminate green; lower sepal nearly round, 14 mm. in diameter, petaloid, asymmetrically funnel form, cuspidate, colorless infused with red; green apex with a hollow spur, red 47B, very tip green; 55 mm. long if full grown.

(E) *Flowers borne.*—On pedicels, 60 mm. long, colorless but infused with red.

(F) *Quantity of flowers.*—One flower per leaf, occurring progressively around the whorl of leaves.

(G) *Petals.*—(1) Shape: Top petal heart-shaped with wide base; lower petals heart-shaped. (2) Color: Newly opened flowers are close to 40D or 33B, with a light "eye" and a red stripe at the base of each of the 2 lower petals; mature flowers fade to 33C, and nearly decomposed petals are approximately 33D; under side red 41C. (3) Number: Five, the four lower petals being united in lateral pairs. (4) Size of petals: Top petal 25 mm. long × 30 mm. wide; 2 middle petals 30 mm. long × 22 mm. wide; 2 lower petals 35 mm. long × 30 mm. wide. Flower 60 mm. in total diameter.

(H) *Reproductive organs.*—(1) Stamens: Five in number, with the lower stamen being shorter than the others. (a) Anthers: hooded shape, cream in color with red shading. (b) Pollen color: cream. (c) Stamens united in an asymmetrical tube, covering the ovary. (2) Pistels: (a) Stigma shape: five pointed star, colorless. (b) Style: very short, dome shaped, colorless. (c) Ovary: 5 celled, 5 mm. long, green in color, explosively dehiscent.

Disease resistance: No general plant diseases observed to date. However, two dotted spider mite can cause plant injury, and thrips can cause injury and stunting of the growing tip.

We claim:

1. A new and distinct cultivar of impatiens known by the cultivar name Halo, as described and illustrated, and particularly characterized as to novelty by the combined characteristics of good self-branching; spreading habit; highly variegated foliage; bright orange and large flowers; early flowering; suitability for growing both outside in full sunlight and in hanging baskets; and by its good keeping quality both outside in full sunlight and in hanging baskets.

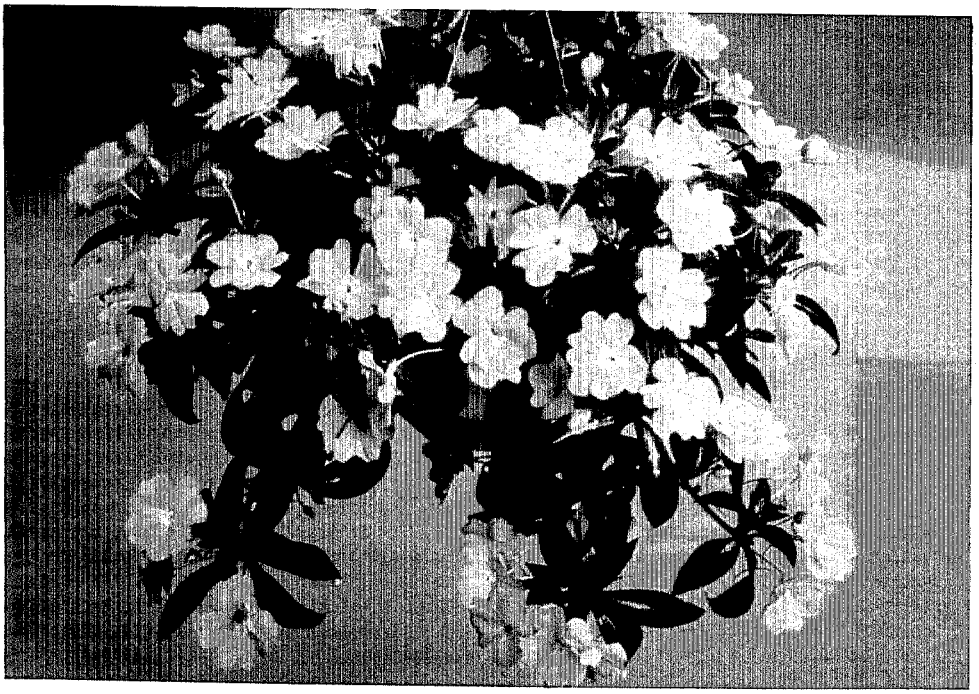

* * * * *